(12) United States Patent
Buehler et al.

(10) Patent No.: US 9,122,929 B2
(45) Date of Patent: Sep. 1, 2015

(54) METHOD OF IDENTIFYING A TRACKED OBJECT FOR USE IN PROCESSING HYPERSPECTRAL DATA

(75) Inventors: Eric Daniel Buehler, Grand Rapids, MI (US); Benjamin Thomas Occhipinti, Grand Rapids, MI (US); Konrad Robert Kuczynski, Grand Rapids, MI (US)

(73) Assignee: GE Aviation Systems, LLC, Grand Rapids, MI (US)

( * ) Notice: Subject to any disclaimer, the term of this patent is extended or adjusted under 35 U.S.C. 154(b) by 274 days.

(21) Appl. No.: 13/588,568

(22) Filed: Aug. 17, 2012

(65) Prior Publication Data

US 2014/0050352 A1  Feb. 20, 2014

(51) Int. Cl.
  *G06K 9/00* (2006.01)
  *G01N 21/359* (2014.01)
  *G01J 3/02* (2006.01)

(52) U.S. Cl.
  CPC .......... *G06K 9/0063* (2013.01); *G01J 3/02* (2013.01); *G01N 21/359* (2013.01)

(58) Field of Classification Search
  CPC ... G06T 7/10; G06T 2207/10024; G06K 9/62
  USPC ......... 382/100, 103–107, 276, 293–294, 154, 382/285; 345/419; 348/169–172, 42–60; 700/1; 707/600, 687
  See application file for complete search history.

(56) References Cited

U.S. PATENT DOCUMENTS

| | | | |
|---|---|---|---|
| 5,559,496 A * | 9/1996 | Dubats | 340/539.26 |
| 6,985,172 B1 * | 1/2006 | Rigney et al. | 348/149 |
| 2004/0130620 A1 * | 7/2004 | Buehler et al. | 348/143 |
| 2007/0224694 A1 * | 9/2007 | Puchalski | 436/171 |
| 2008/0046217 A1 * | 2/2008 | Polonskiy et al. | 702/179 |
| 2008/0129581 A1 * | 6/2008 | Douglass et al. | 342/52 |
| 2011/0089323 A1 * | 4/2011 | Treado et al. | 250/330 |
| 2011/0229056 A1 * | 9/2011 | Robertson et al. | 382/294 |
| 2012/0274775 A1 * | 11/2012 | Reiffel | 348/158 |
| 2013/0034266 A1 * | 2/2013 | Shamir et al. | 382/103 |
| 2014/0050406 A1 * | 2/2014 | Buehler et al. | 382/191 |

OTHER PUBLICATIONS

Lawrence E. Hoff ; Edwin M. Winter; Spectrally assisted target tracking. Proc. SPIE 8137, Signal and Data Processing of Small Targets 2011, 81370Z (Sep. 16, 2011); doi:10.1117/12.895416.*

Dimitris Manolakis et al., Hyperspectral Image Processing for Automatic Target Detection Applications, vol. 14, No. 1, 2003, Lincoln Laboratory Journal.

* cited by examiner

*Primary Examiner* — Hadi Akhavannik
(74) *Attorney, Agent, or Firm* — General Electric Company; William S. Munnerlyn

(57) ABSTRACT

The invention relates a method of identifying a tracked object that has a known database of hyperspectral and spatial information. The method associates an identifier with the tracked object; selects a parameter associated with the hyperspectral or spatial information of the tracked object; detects a deviation in the selected parameter; compares the deviation with the database; and if the deviation exceeds a predetermined threshold, assigns a new identifier to the tracked object, and if the deviation does not exceed the predetermined threshold, continues tracking the tracked object.

15 Claims, 5 Drawing Sheets

METHOD OF IDENTIFYING A TRACKED OBJECT FOR USE IN PROCESSING HYPERSPECTRAL DATA

BACKGROUND OF THE INVENTION

The environment of a remote sensing system for hyperspectral imagery (HSI) is well described in "Hyperspectral Image Processing for Automatic Target Detection Applications" by Manolakis, D., Marden, D., and Shaw G. (Lincoln Laboratory Journal; Volume 14; 2003 pp. 79-82). An imaging sensor has pixels that record a measurement of hyperspectral energy. An HSI device will record the energy in an array of pixels that captures spatial information by the geometry of the array and captures spectral information by making measurements in each pixel of a number of contiguous hyperspectral bands. Further processing of the spatial and spectral information depends upon a specific application of the remote sensing system.

Remotely sensed HSI has proven to be valuable for wide ranging applications including environmental and land use monitoring, military surveillance and reconnaissance. HSI provides image data that contains both spatial and spectral information. These types of information can be used for remote detection and tracking tasks. Specifically, given a set of visual sensors mounted on a platform such as an unmanned aerial vehicle (UAV) or ground station, a video of HSI may be acquired and a set of algorithms may be applied to the spectral video to detect and track objects from frame to frame.

Spectral-based processing algorithms have been developed to classify or group similar pixels; that is, pixels with similar spectral characteristics or signatures. Processing in this manner alone is not amenable to target tracking and detection applications where the number and size of targets in a scene is typically too small to support the estimation of statistical properties necessary to classify the type of target. However, spatial processing of typical HSI is compromised by the low spatial resolution of typical systems that collect HSI. As a result, remote sensing systems that collect and process HSI are typically developed as a trade-off between spectral and spatial resolution to maximize detection of both resolved and unresolved targets where a resolved target is an object imaged by more than one pixel. In this way, spectral techniques can detect unresolved targets by their signature and spatial techniques can detect resolved targets by their shape.

A number of hyperspectral search algorithms have been developed and used in the processing of HSI for the purpose of target detection. These hyperspectral search algorithms are typically designed to exploit statistical characteristics of candidate targets in the imagery and are typically built upon well-known statistical concepts. For example, Mahalanobis distance is a statistical measure of similarity that has been applied to hyperspectral pixel signatures. Mahalanobis distance measures a signature's similarity by testing the signature against an average and standard deviation of a known class of signatures.

Other known techniques include Spectral Angle Mapping (SAM), Spectral Information Divergence (SID), Zero Mean Differential Area (ZMDA) and Bhattacharyya Distance. SAM is a method for comparing a candidate target's signature to a known signature by treating each spectra as vectors and calculating the angle between the vectors. Because SAM uses only the vector direction and not the vector length, the method is insensitive to variation in illumination. SID is a method for comparing a candidate target's signature to a known signature by measuring the probabilistic discrepancy or divergence between the spectra. ZMDA normalizes the candidate target's and known signatures by their variance and computes their difference, which corresponds to the area between the two vectors. Bhattacharyya Distance is similar to Mahalanobis Distance but is used to measure the distance between a set of candidate target signatures against a known class of signatures.

BRIEF DESCRIPTION OF THE INVENTION

The invention relates to a method of identifying a tracked object. The method comprises tracking an object using an image sensor, wherein the tracked object has a known database of hyperspectral and spatial information; associating an identifier with the tracked object; selecting at least one parameter associated with the hyperspectral or spatial information of the tracked object; detecting a deviation in the selected at least one parameter; comparing the deviation with the database; and if the deviation exceeds a predetermined threshold, assigning a new identifier to the tracked object, and if the deviation does not exceed the predetermined threshold, continue tracking the tracked object.

DESCRIPTION OF EMBODIMENTS OF THE INVENTION

Figure 1:
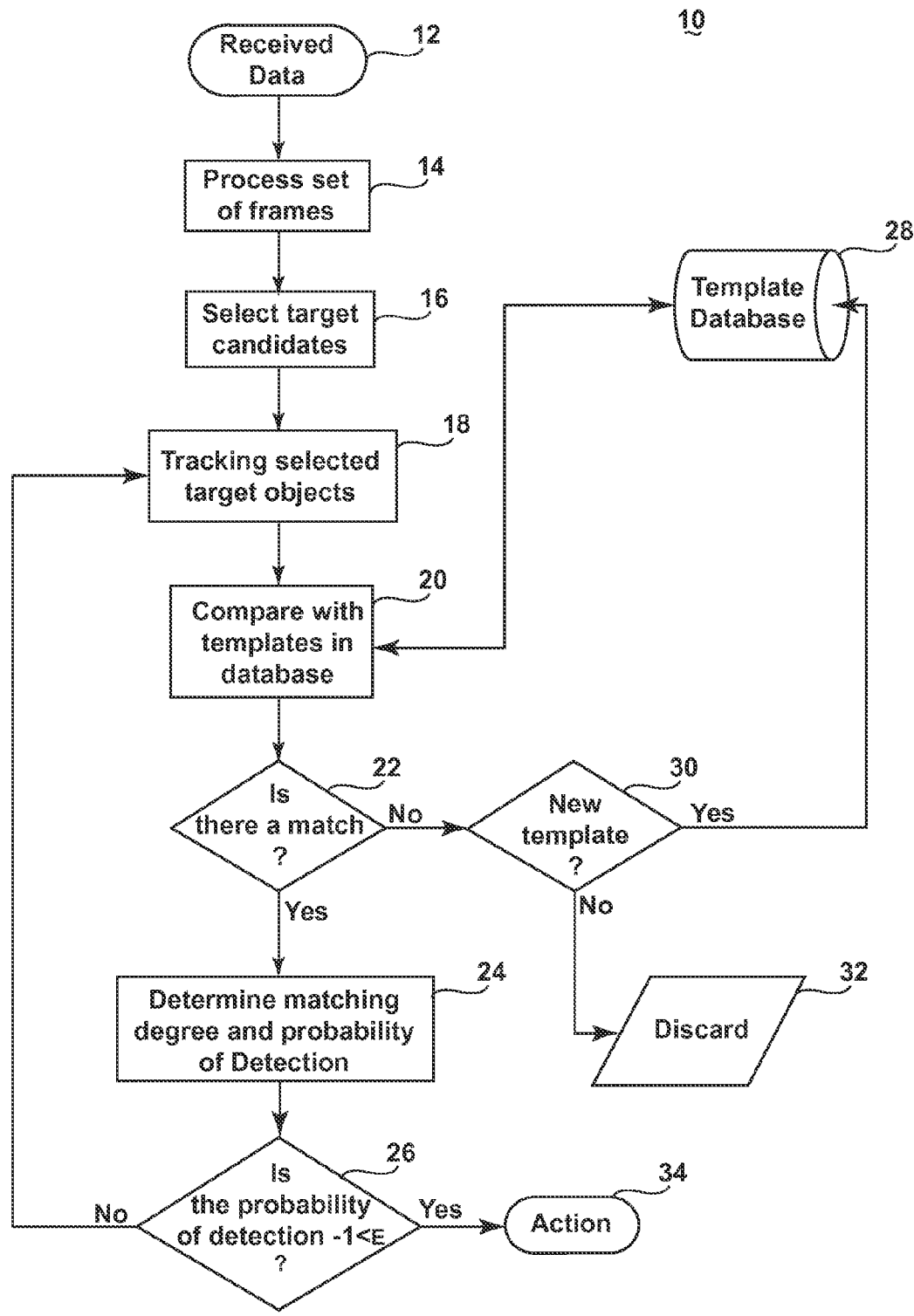
FIG. 1 is a diagrammatic view of a method for tracking and determining a probability of detection for observed objects in HSI according to a first embodiment of the invention.

In the background and the following description, for the purposes of explanation, numerous specific details are set forth in order to provide a thorough understanding of the technology described herein. It will be evident to one skilled in the art, however, that the exemplary embodiments may be practiced without these specific details. In other instances, structures and device are shown in diagram form in order to facilitate description of the exemplary embodiments.

The exemplary embodiments are described with reference to the drawings. These drawings illustrate certain details of specific embodiments that implement a module, method, or computer program product described herein. However, the drawings should not be construed as imposing any limitations that may be present in the drawings. The method and computer program product may be provided on any machine-readable media for accomplishing their operations. The embodiments may be implemented using an existing computer processor, or by a special purpose computer processor incorporated for this or another purpose, or by a hardwired system.

As noted above, embodiments described herein may include a computer program product comprising machine-readable media for carrying or having machine-executable instructions or data structures stored thereon. Such machine-readable media can be any available media, which can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium that can be used to carry or store desired program code in the form of machine-executable instructions or data structures and that can be accessed by a general purpose or special purpose computer or other machine with a processor. When information is transferred or provided over a network or another communication connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data, which cause a general purpose computer, special purpose computer, or special purpose processing machines to perform a certain function or group of functions.

Embodiments will be described in the general context of method steps that may be implemented in one embodiment by a program product including machine-executable instructions, such as program code, for example, in the form of program modules executed by machines in networked environments. Generally, program modules include routines, programs, objects, components, data structures, etc. that have the technical effect of performing particular tasks or implement particular abstract data types. Machine-executable instructions, associated data structures, and program modules represent examples of program code for executing steps of the method disclosed herein. The particular sequence of such executable instructions or associated data structures represent examples of corresponding acts for implementing the functions described in such steps.

Embodiments may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the internet and may use a wide variety of different communication protocols. Those skilled in the art will appreciate that such network computing environments will typically encompass many types of computer system configuration, including personal computers, hand-held devices, multiprocessor systems, microprocessor-based or programmable consumer electronics, network PCs, minicomputers, mainframe computers, and the like.

Embodiments may also be practiced in distributed computing environments where tasks are performed by local and remote processing devices that are linked (either by hardwired links, wireless links, or by a combination of hardwired or wireless links) through a communication network. In a distributed computing environment, program modules may be located in both local and remote memory storage devices.

An exemplary system for implementing the overall or portions of the exemplary embodiments might include a general purpose computing device in the form of a computer, including a processing unit, a system memory, and a system bus, that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD-ROM or other optical media. The drives and their associated machine-readable media provide nonvolatile storage of machine-executable instructions, data structures, program modules and other data for the computer.

Technical effects of the method disclosed in the embodiments include increasing the utility and performance of hyperspectral signature matching, especially when object detection and tracking methods are used in conjunction with the method. The method lowers the amount of man hours necessary to observe a tracked target. As well, the method improves on the autonomous identification and association of new objects, related to ones already tracked, prevents the loss of tracking and extends autonomous tracking by removing the need for instant review by a human operator. This technique can be used on any system that generates composite imagery from spectral cube arrays.

FIG. 1 is a diagrammatic view of a method 10 for tracking and determining a probability of detection for observed objects in HSI according to a first embodiment of the invention. Remotely sensed HSI that may include single images or a hyperspectral video feed may be input at 12 to a processor capable of processing the HSI. The processor receives the hyperspectral data at 12 and processes the data set into a set of hyperspectral image frames at 14 by performing a series of well-known image processing steps that may include but not be limited to noise filtering, corner detection, image registration, homography and frame-to-frame alignment. The processor may then select candidate targets using search algorithms at 16 from tracked objects in the hyperspectral image frames, where candidate targets and tracked objects are sets of pixels that may represent the hyperspectral image of a real-world object of interest. For example, in a system collecting HSI that is designed to search for moving targets, candidate targets may be moving objects. In this example, the processor may perform a computational search for the minimum discriminant characteristics that identify moving objects in HSI. In another example, a user of a system collecting HSI manually selects pixels on a display and identifies the corresponding signatures for further analysis.

The processor may then track selected candidate targets at 18 from frame to frame of the HSI. The processor may compare at 20 the selected candidate targets to reference target templates of known targets stored in a template database at 28 where reference target templates are sets of pixels that may have been previously established to represent the hyperspectral image of a real-world object of interest.

At 22, the processor may make a match comparison. If a selected candidate target matches a reference target template from the template database at 28, the processor at 24 may then determine a matching degree between the selected candidate target and a reference target template, and a probability that the selected candidate target has been detected. If the selected candidate target does not match a template, then the processor may either consider the selected candidate target to be a new reference target template at 30 or discard it at 32. If the selected candidate target is considered a new template at 30, then the processor may add data relating to the new target to the target template database at 28.

After the determination of the matching degree and the probability of detection at 24, the processor may compare the probability to a threshold at 26. If the probability exceeds a threshold, the processor may take an action at 34. Otherwise, the processor may continue to track the selected candidate target at 18.

After specific reference target templates are identified from the reference target template database at 28 and compared at 20 with the candidate targets, the processor may calculate the matching degree and probability of detection at 24. The matching degree and probability of detection may measure the probability of the selected candidate target to be a match to a specific reference target template by first comparing at 24 the top spectral signatures that appear in the selected candidate target with the top spectral signatures that define the reference target template and then matching them spatially.

The processor computing the method of determining the matching degree and probability of detection at 24 may first determine the set of top signatures appearing in both the selected candidate target and the reference target template. Then, the processor may calculate the distribution of those top signatures based on the number of pixels in both the selected candidate target and the reference target template. To do this, the first step is to determine the set of signatures in the reference target template that cover a certain percentage of the pixels in the reference target template and determine the percentage of each one of the signatures in the reference target template. The processor computing the method at 24 may then determine the distribution of signatures for a selected candidate target. If the distribution of pixels in each signature is similar to the distribution of signatures in the reference target template, then processor computing the method may calculate the matching degree for each one of the signatures considering the maximum and the minimum difference between similar signature pixels. The processor computing the similarity between hyperspectral pixel distributions may employ one or more measures of similarity for the computation. Similarity measures may include SAM, SID, ZMDA or Bhattacharyya Distance. The processor may employ other similarity measures depending upon the implementation.

Let $S_i=\{s_1, s_2, \ldots, s_p\}$ be the set of signatures in a target, and let $x_{ij}$, be a pixel in the ij location in the two dimensional spatial representation of a hyperspectral frame. The pixel $x_{ij}$ is made up of an array of subpixels such that the pixel $x_{ij}$ has a set of values $x_{b1}, x_{b2}, \ldots, x_{bq}$ where q is the number of spectral bands in the hyperspectral imagery. Therefore, each pixel contains a subpixel value associated with each spectral band for the spatial location described by the pixel.

A selected candidate target referenced here for brevity as object $O_i$ that spatially matches reference template target referenced here for brevity as target T may also spectrally match target T with confidence C if the set of R % top signatures in target T appear in a λ similar proportion in object $O_i$. The goal is to match the object and the target spatially and spectrally, that is the shapes and the signatures of the object and target are similar.

Let $N_i$ be the number of pixels in object $O_i$ and $n_{i1}$, $n_{i2}, \ldots, n_{ir}$ with r<p defining the cardinality or size of the sets of pixels in object $O_i$ that present similar signatures $s_1$, $s_2, \ldots, s_r$. The processor computing the method at 24 considers two objects $O_i$ and $O_j$ a spectral match if the top R % of the spectral signatures in object $O_i$ match the R % top signatures of object $O_j$. The two objects $O_i$ and $O_j$ λ-match precisely if for all the selected number of top signatures of object $O_i$ and $O_j$ denoted as $\{n_{i1}, n_{i2}, \ldots, n_{ir}\}$ and $\{n_{j1}, n_{j2}, \ldots, n_{jr}\}$ respectively:

$$\left|\frac{n_{i1}}{N_i} - \frac{n_{j1}}{N_j}\right| < \lambda$$

$$\left|\frac{n_{i2}}{N_i} - \frac{n_{j2}}{N_j}\right| < \lambda$$

$$\vdots$$

$$\left|\frac{n_{ir}}{N_i} - \frac{n_{jr}}{N_j}\right| < \lambda$$

The matching degree for each signature l may be defined as:

$$\eta_l(O_i, O_j) = 1 - |\max_l |x_{il} - x_{ijl}| - \min_l |x_{il} - x_{ijl}||$$

The method may employ other definitions for the matching degree for each signature, l. Any definition to determine matching degree at 24 must conform to the well-known mathematical definition of a fuzzy measure.

Finally, the processor computing the method at 24 may calculate a probability of detection based on the similarity between the set of signatures in the template and the set of signatures in the object. Considering $N_i$ number of pixels in object $O_i$ and $N_j$ number of pixels in object $O_j$, the processor may calculate the probability of detection at 24 based on the matching degree and the number of pixels that match each signature. The processor may calculate the probability of detection by normalizing the matching degree to the number of pixels of the object to determine a confidence level of how close the image of the selected candidate target object matches the hyperspectral image reference target template. The probability of detection, referenced as TM, is computed as:

$$TM = \frac{\sum_s \eta_l * N_i \big|_s}{\sum_s N_i \big|_s}$$

where $N_i|s$ number of pixels in $O_i$ λ-match the signature s.

At 26, the probability of detection or TM for a selected candidate target object as a match for a target template may be compared to a threshold. As shown at 26, the processor may calculate TM−1 and compare to threshold, ϵ. If the quantity TM−1 exceeds threshold, ϵ, the processor may take an action at 34. Otherwise, the processor may continue to track the selected candidate target at 18. The value of the threshold, ϵ, may be selected based upon the specific implementation of the matching algorithm at 22, the search algorithm at 16 and information pertaining to the specific candidate target and reference target template in the database at 28 such as the calculated object velocity in the scene of the HSI.

Different levels of confidence are defined based on the value of TM. For example, in an instance, if TM is less than 0.35 the confidence level will be very low; if TM is between 0.35 and 0.60, the level of confidence will be low, if TM is between 0.60 and 0.75, the level of confidence will be medium; if TM is between 0.75 and 0.85, the level of confidence will be medium-high; and if TM is greater than 0.85, the level of confidence will be high. As the probability of a match becomes more likely, a display of the results may iterate through a series of colors mapped to these levels of TM to distinguish targets detected with a high level of confidence from targets detected with a low level of confidence. The pixels of an image of a target detected with a high level of confidence may, for example, all be colored red on a display. Other thresholds, levels of confidence and displays schemes may be used depending upon the implementation.

Figure 2:
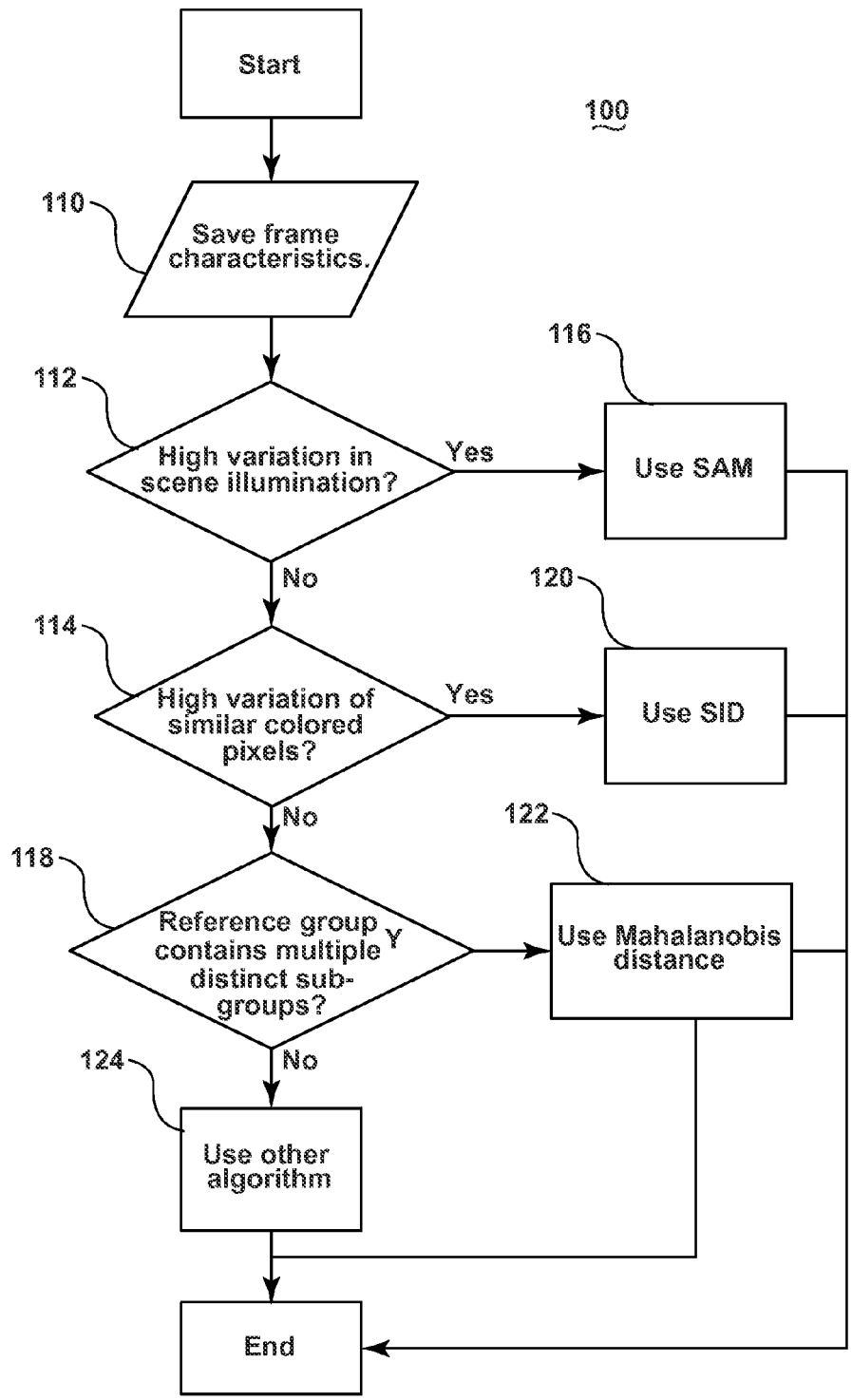
FIG. 2 is a diagrammatic view of a method for selecting a hyperspectral search algorithm according to an embodiment of the invention.

When the processor receives data at 12 and processes it into a set of hyperspectral frames at 14, the processor may then select candidate targets at 16 from the hyperspectral frames. The processor may select and use a search algorithm for hyperspectral data for selecting the candidate targets at 16. The dimension of the hyperspectral data may have been reduced by means of well-known dimensionality reduction techniques, including but not limited to principal components analysis, feature extraction, and entropy measurements. FIG. 2 is a diagrammatic view of a method 100 for selecting a search algorithm for hyperspectral data according to an embodiment of the invention. To select a search algorithm for hyperspectral data, a processor computing the method at 100 may initially save characteristics of a hyperspectral frame to a database at 110. Next, the processor may assess a characteristic of the hyperspectral frame at 112. If the processor assesses the characteristic at 112 to be of significance for the hyperspectral frame, the processors may apply a search algorithm to the data at 116 to distinguish the candidate targets of the frame. If the processor assesses the characteristic at 112 to not be significant for the hyperspectral frame, the processor may assess a second characteristic at 114. If the processor assesses the second characteristic at 114 to be of significance for the hyperspectral frame, the processor may apply a second spectral search algorithm at 120 to the data to distinguish the candidate targets of the frame. If the processor assesses the second characteristic at 114 to not be significant for the frame, the processor may assess a third characteristic at 118. If the processor assesses the third characteristic at 118 to be of significance for the hyperspectral frame, the processor may apply a third search algorithm at 122 to the data to distinguish the candidate targets of the hyperspectral frame. If processor assesses the third characteristic at 118 to not be significant for the hyperspectral frame, the processor may apply a default search algorithm 124 to the data.

Initially, the processor may determine characteristics of a hyperspectral frame at 110. The processor may save the hyperspectral frame characteristics at 110 such that they are available for further processing when selecting a search algorithm. Example characteristics may include an estimate of the variability of the illumination of imaged scene, the variability of pixels with similar signatures, and the number of distinct signatures in the reference target template. Other characteristics of the hyperspectral frame may be considered and these examples should not be considered limiting.

Based upon an assessment of the first characteristic at 112 of the hyperspectral frame, the processor may apply a search algorithm that has been proven to work well with hyperspectral data characterized by that first characteristic at 116. If the assessment of the first characteristic at 112 of the hyperspectral frame does not indicate the first search algorithm will work well with the hyperspectral frame, the processor may access the saved frame characteristics from 110 for an assessment of a second frame characteristic at 114. In one example, the first characteristic may be the variability of the illumination of the imaged scene of the hyperspectral frame. The processor may access the hyperspectral frame characteristics to determine the variability of the illumination of the imaged scene. The processor may make a decision to determine if the variability is high or low. The processor may use other frame characteristics as a first frame characteristic depending upon the implementation.

If the first hyperspectral frame characteristic is assessed to be of significance, the processor may use a first search algorithm at 116 to process the hyperspectral frame and its candidate targets. In this example, if the processor calculates high variability of the illumination of the imaged scene, a search algorithm based upon SAM may process the imaged scene for optimal results. The method may use other search algorithms based upon classification methods including but not limited to SID, Mahalanobis Distance, ZMDA and Bhattacharyya Distance, depending upon the implementation.

Based upon an assessment of the second characteristic at 114 of the hyperspectral frame, the processor may apply a search algorithm that is known to work well with hyperspectral data characterized by that second characteristic at 120. If the assessment of the second characteristic at 114 of the hyperspectral frame does not indicate the second search algorithm will work well with the hyperspectral frame, the processor may access the saved frame characteristics from 110 for an assessment of a third frame characteristic at 118. In one example, the second characteristic may be the variability of pixels with similar signatures. The processor may access the hyperspectral frame characteristics to determine the variability of pixels with similar signatures. The processor may make a decision to determine if the variability is high or low. The processor may use other frame characteristics as a second frame characteristic depending upon the implementation.

If the second hyperspectral frame characteristic is assessed to be of significance, the processor may use a second search algorithm at 120 to process the hyperspectral frame and its candidate targets. In this example, if the processor calculates high variability of the pixels with similar signatures, a search algorithm based upon SID may process the imaged scene for optimal results. The method may use other search algorithms based upon similarity or distance measures, including but not limited to SAM, Mahalanobis Distance, ZMDA and Bhattacharyya Distance, depending upon the implementation.

Based upon an assessment of the third characteristic at 118 of the hyperspectral frame, the processor may apply a search algorithm that is known to work well with hyperspectral data characterized by that third characteristic at 122. If the assessment of the third characteristic at 118 of the hyperspectral frame does not indicate the third search algorithm will work well with the hyperspectral frame, the processor may apply a default search algorithm at 124 to process the hyperspectral frame. In one example, the third characteristic may be the number of distinct signatures in the reference target template. The processor may access the hyperspectral frame characteristics including previously tracked targets and corresponding reference target templates to determine the number of distinct signatures in the reference target template. The processor may make a decision to determine if the number of distinct signatures in the reference target template is high or low. The processor may use other frame characteristics as a third frame characteristic depending upon the implementation.

If the third hyperspectral frame characteristic is assessed to be of significance, the processor may use a third search algorithm at 122 to process the hyperspectral frame and its candidate targets. In this example, if the processor calculates a high number of distinct signatures in the reference target template, a search algorithm based upon Mahalanobis Distance may process the imaged scene for optimal results. The method may use other search algorithms based upon similarity or distance measures, including, but not limited to SAM, SID, ZMDA and Bhattacharyya Distance, depending upon the implementation.

Upon exhaustion of the frame characteristics, the processor may use a default search algorithm at 124 to process the hyperspectral frame and its candidate targets. The default search algorithm may be based upon any of SAM, SID, Mahalanobis Distance, ZMDA and Bhattacharyya Distance. The method may use other search algorithms as a default search algorithm depending upon the implementation.

The method at 100 may implement additional steps using other frame characteristics and their assessments. Frame characteristics may be daisy-chained into decision steps that follow the previously disclosed decision steps at 112, 114, and 118. Also, the processor may assess multiple frame characteristics to determine if a particular search algorithm is optimally deployed to process the hyperspectral frame.

The method at 100 may implement additional search algorithms. For example, the processor may run multiple search algorithms on the hyperspectral frame concurrently. The processor may then aggregate the results using multicriteria decision making methodologies from the concurrent processing of multiple search algorithms into a single result.

Figure 3:
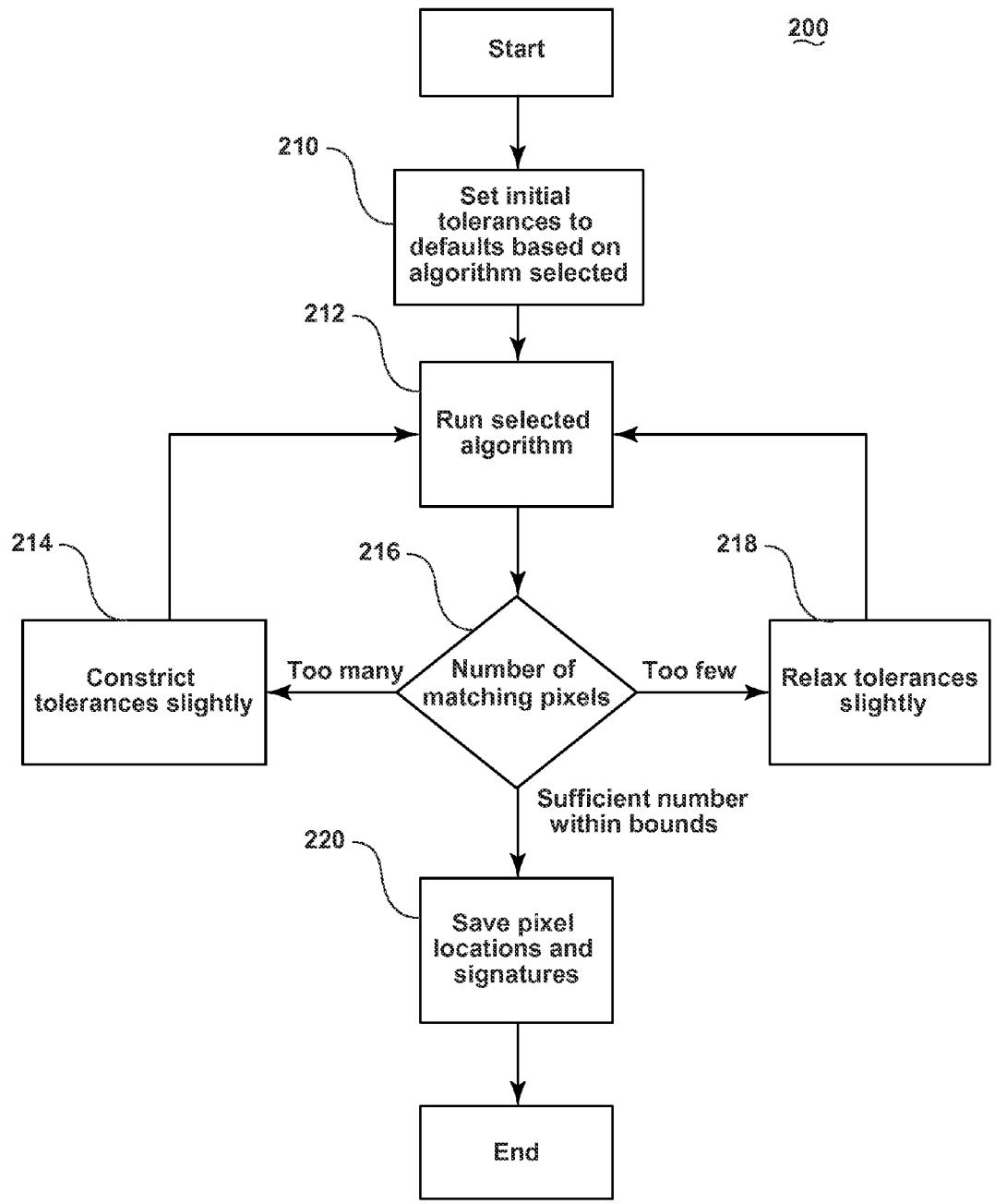
FIG. 3 is a diagrammatic view of a method for selecting a tolerance for a hyperspectral search algorithm according to an embodiment of the invention.

FIG. 3 is a diagrammatic view of a method at 200 for selecting a tolerance for a search algorithm. When processing the hyperspectral frame with a selected search algorithm at 116, 120, 122 and 124 in FIG. 2, the parameters or tolerances of the given algorithm may be initially set to a default value or values at 210. The search algorithm may then process the data from the hyperspectral frame along with the default tolerances at 212. The selected search algorithm may compute the number of hyperspectral pixels from the hyperspectral frame that are determined to match the candidate targets from the hyperspectral frame to the reference target template at 216. If too few hyperspectral pixels match the candidate targets from the hyperspectral frame to the reference target template, the processor may relax the tolerances for the selected search algorithm at 218 and then the search algorithm may then process the hyperspectral frame again at 212 with the modified tolerances. If too many hyperspectral pixels match the candidate targets from the hyperspectral frame to the reference target template, the processor may constrict the tolerances for the selected search algorithm at 214 and then the search algorithm may then process the hyperspectral frame again at 212 with the modified tolerances. If an acceptable number of hyperspectral pixels match, the processor may save the location and signatures of the matching hyperspectral pixels at 220.

The processor may repeat the steps of modifying the tolerances of the search algorithm at 214 and 218 followed by processing the hyperspectral frame with the selected search algorithm at 212 until the matching number of pixels at 216 lies within acceptable bounds.

The method at 10 in FIG. 1 for tracking and determining a probability of detection for observed objects in HSI according to a first embodiment of the invention may instruct an action at 34 in FIG. 1 based upon the probability of detection for a candidate target exceeding a threshold at 26 in FIG. 1 based upon analysis of the spectral and spatial parameters of the candidate target relative to known templates in the reference target template database at 28. At this point, each candidate target may have a unique identifier associated with it. If the processor computing the method at 10 of FIG. 1 detects deviation in a candidate target based upon changes in its spectral and spatial characteristics, the processor may then autonomously mark the deviation as a significant event in that target's lifecycle. The processor may then allocate an identifier to identify the deviated target as a new object. The processor may aggregate all target events into a reviewable timeline, where a human operator has the ability to evaluate and potentially correct the processor's choice of associating new or existing identifiers to the tracked objects.

The processor computing the method at 10 in FIG. 1 may create an entry in the target template database at 28 in FIG. 1 with descriptions of both the hyperspectral and spatial information and characteristics of the candidate target at the point of target selection at 16 in FIG. 1. In addition to hyperspectral and spatial information, the target template database at 28 in FIG. 1 may also store information about time as the processor tracks the candidate target in the HSI. If the processor detects a deviation in the spectral or spatial parameters at 20 in FIG. 1 used to track a candidate target, the processor may store information in the database at 28 in FIG. 1 that classifies the change as an event that may be used for future review. Additionally, the processor may associate either the same or a new, unique identifier to the new object whose defined parameters are appreciably different than the original target. The processor may base the decision to assign an event on a calculated confidence measurement for determining a significant deviation from the established parameters. The confidence measurement may use parameters defined in spatial, spectral or both domains to be robust to sensing errors in the hyperspectral and spatial information.

There are many scenarios where a candidate target's parameters may significantly deviate from its previously established parameters and trigger an event. Such scenarios may include; a tracked object becomes occluded by another object; a tracked object splits into multiple separate objects; a tracked object significantly changes its spectral characteristics, such as color, contrast, or brightness by traversing into an area covered in shadow. Other scenarios exist and these should not be considered limiting. If the processor cannot associate a candidate target before and after such an event, the processor may associate the same identifier used for the candidate target before the event to the one or more new candidate targets after the event, removing the possibility of losing or mislabeling a target.

Figure 4A:
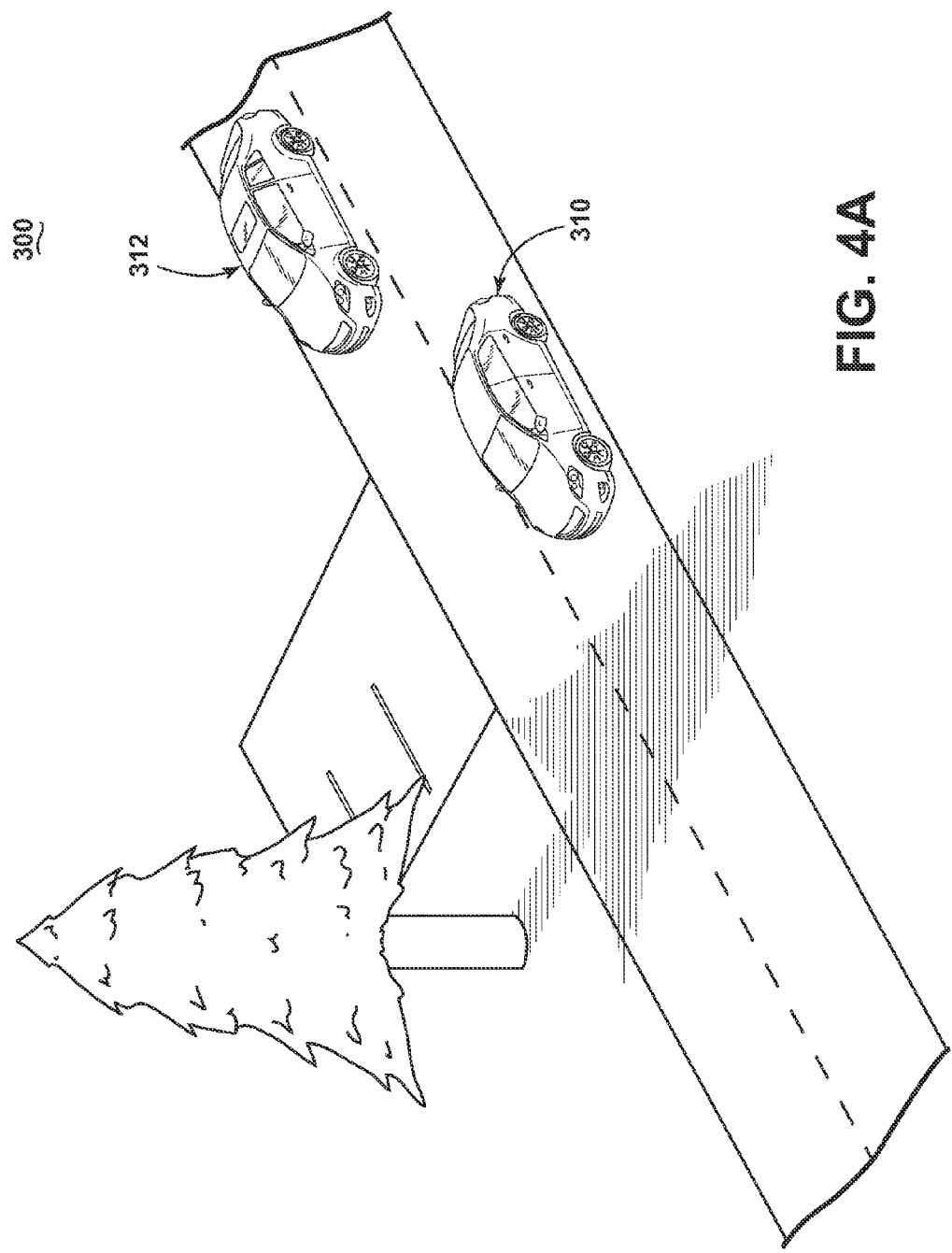
FIG. 4a shows a scenario where a hyperspectral imaging system according to an embodiment of the invention has detected and tracked two objects.
Figure 4B:
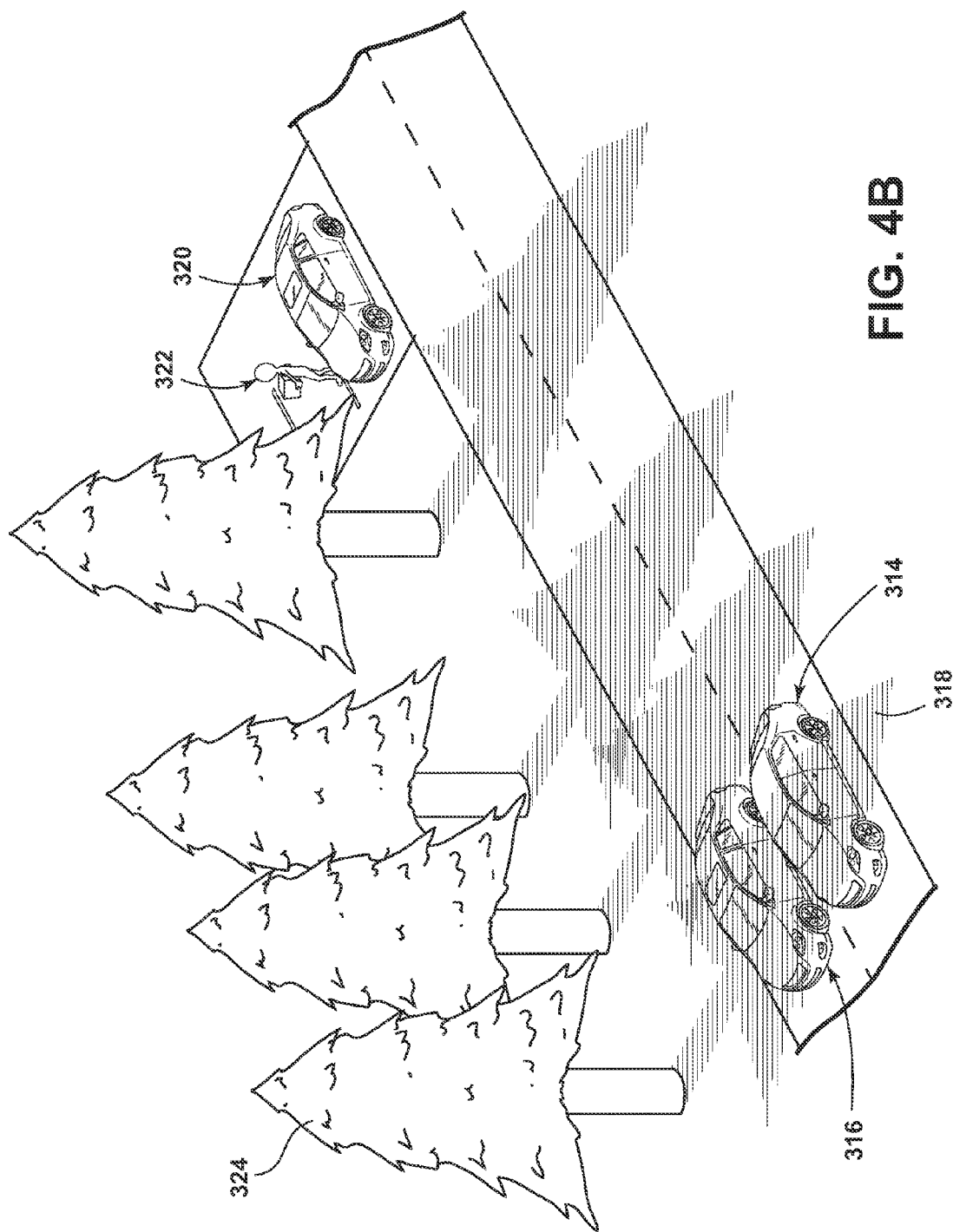
FIG. 4b shows a scenario where a hyperspectral imaging system according to an embodiment of the invention detects changes in tracked objects.

FIGS. 4a and 4b demonstrate one such example scenario. FIG. 4a shows an example scenario at 300 where the method for tracking and determining a probability of detection for observed objects in HSI according to an embodiment of the invention has detected and tracked two vehicles 310, 312 traveling on a road. The processor implementing the method at 10 in FIG. 1 processes the received hyperspectral data at 12 in FIG. 1 into a sequence of hyperspectral frames at 14 in FIG. 1 to select candidate targets at 16 in FIG. 1. Upon a comparison of the candidate targets at 20 in FIG. 1 with templates in the reference target template database at 28 in FIG. 1, the resulting calculations of degree of matching and probability of detection at 24 in FIG. 1 are significant and trigger action at 34 in FIG. 1. The processor assigns each car 310, 312 a target identifier that may be stored in the reference target template database at 28 in FIG. 1.

FIG. 4b shows a scenario where the method for tracking and determining a probability of detection for observed objects in HSI according to an embodiment of the invention has detected changes in tracked objects. FIG. 4b demonstrates an event whereby one of the previously identified candidate targets, a car 310 in FIG. 4A travels under the shadow 318 of a tree 324 thereby significantly changing the spectral characteristics of the tracked car 310 in FIG. 4A. Additionally, a second similar car is now traveling next to the previously tracked car 310 in FIG. 4A. The processor computing the method as 10 in FIG. 1 may now distinguish with low confidence which car 314 or 316 is the previously tracked and identified car 310 in FIG. 4A. The processor may take the action at 34 in FIG. 1 to identify both cars 314 and 316 with identifiers that may be associated with the previously tracked car's identifier and log the time of the event into the database at 28 in FIG. 1 for both objects.

The second of the previously identified candidate targets, a car 312 in FIG. 4A stops at a parking lot and a passenger 322 exits the now stopped vehicle 320. The processor may detect and identify an event whereby the original object of the car 312 in FIG. 4A has split into two separately trackable objects. The processor may take the action as 34 in FIG. 1 to identify both car 320 and person 322 with identifiers that may be associated with the car 312 in FIG. 4A prior to the event and to log the time of the event into the database at 28 in FIG. 1.

A benefit to storing the information about event and creating identifiers that may be associated with events is that an operator of the system may recall the event history of any target associated with any target identifier. The operator then may analyze all the objects with that identifier or associated identifiers that are being tracked along with the object's history for review. The event history may include all the data relating to all of the events where the system altered identifier's for tracked objects. Additionally, the operator could manually correct the system if the identifier that was associated with a target or targets at an event is incorrect.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of identifying a tracked object comprising:
   tracking an object using at least one image sensor, the tracked object corresponding to a predetermined identifier associated with hyperspectral and spatial information maintained in at least one database;
   selecting at least one parameter associated with the hyperspectral or spatial information of the tracked object;
   detecting a deviation in the selected at least one parameter;
   comparing the deviation with the hyperspectral and spatial information associated with predetermined identifier; and
   in response to the deviation exceeding a predetermined threshold, assigning a new identifier to the tracked object.

2. The method of claim 1, further comprising updating the predetermined identifier based on the deviation in the at least one parameter.

3. The method of claim 1, further comprising identifying the deviation in the selected at least one parameter as a target event.

4. The method of claim 1, wherein the at least one parameter includes at least one of color, contrast, brightness, shape, velocity, direction, size, or location.

5. The method of claim 1, wherein the comparing the deviation with the hyperspectral and spatial information associated with predetermined identifier includes using at least one of Spectral Angle Mapping, Spectral Information Divergence, Zero Mean Differential Angle, Mahalanobis Distance, or Bhattacharyya Distance.

6. The method of claim 1, further comprising continuing tracking the object, in response to the deviation not exceeding the predetermined threshold.

7. The method of claim 3, further comprising including the target event in a timeline of target events associated with at least one of the at least one parameter, tracked object, or predetermined identifier.

8. A method of identifying a tracked object, comprising:
   acquiring a set of hyperspectral and spatial image data;
   generating a set of hyperspectral image frames based on processing the set of hyperspectral and spatial image data;
   selecting a set of candidate targets, corresponding to predetermined reference templates, included in a subset of the hyperspectral image frames;
   tracking the set of candidate targets in the set of hyperspectral image frames;
   generating a matching value by comparing the set of candidate targets and a set of predetermined reference templates;
   determining that the matching value satisfies a predetermined threshold;
   in response to the matching value satisfying the predetermined threshold, generating a new reference template based on the set of candidate targets.

9. The method of claim 8, further comprising:
   determining that the matching value does not satisfy the predetermined threshold; and
   continuing tracking the set of candidate targets, in response to the matching value not satisfying the predetermined threshold.

10. The method of claim 8, wherein the generating the set of hyperspectral image frames includes processing the set of hyperspectral and spatial image data via at least one of noise filtering, corner detection, image registration, homography, or frame-to-frame alignment.

11. The method of claim 8, wherein the selecting the set of candidate targets includes identifying a set of moving objects in the set of hyperspectral image frames, and selecting the set of candidate targets from the set of moving objects.

12. The method of claim 8, wherein the comparing the set of candidate targets and the set of predetermined reference templates, includes comparing a first set of spectral signatures included in the set of candidate targets with a second set of spectral signatures included in the set of predetermined reference templates.

13. The method of claim 12, wherein the comparing the first set of spectral signatures included in the set of candidate targets with the second set of spectral signatures included in the set of predetermined reference templates, includes determining a first distribution of the first set of spectral signatures in the set of candidate targets and a second distribution of the second set of set of spectral signatures in the set of predetermined reference templates, and comparing the first and second distributions.

14. The method of claim 8, further comprising associating a deviation event indicator with the set of candidate targets, in response to the matching value satisfying the predetermined threshold.

15. The method of claim 14, further comprising adding the deviation event indicator to a timeline including a set of indicators.

* * * * *